United States Patent
Park et al.

(10) Patent No.: US 11,844,631 B2
(45) Date of Patent: *Dec. 19, 2023

(54) APPARATUS AND METHOD FOR ESTIMATING BIO-INFORMATION

(71) Applicant: SAMSUNG ELECTRONICS CO., LTD., Suwon-si (KR)

(72) Inventors: Chang Soon Park, Chungju-si (KR); Seung Keun Yoon, Seoul (KR); Dae Geun Jang, Yongin-si (KR)

(73) Assignee: SAMSUNG ELECTRONICS CO., LTD., Suwon-si (KR)

(*) Notice: Subject to any disclaimer, the term of this patent is extended or adjusted under 35 U.S.C. 154(b) by 0 days.

This patent is subject to a terminal disclaimer.

(21) Appl. No.: 17/867,275

(22) Filed: Jul. 18, 2022

(65) Prior Publication Data

US 2022/0346722 A1 Nov. 3, 2022

Related U.S. Application Data

(63) Continuation of application No. 16/874,843, filed on May 15, 2020, now Pat. No. 11,419,557.

(30) Foreign Application Priority Data

Sep. 11, 2019 (KR) .................. 10-2019-0113041

(51) Int. Cl.
*A61B 5/00* (2006.01)
*G16H 50/30* (2018.01)
(Continued)

(52) U.S. Cl.
CPC .......... *A61B 5/7239* (2013.01); *A61B 5/0205* (2013.01); *G16H 40/67* (2018.01);
(Continued)

(58) Field of Classification Search
CPC . A61B 5/7239; A61B 5/0205; A61B 5/02007; A61B 5/021; A61B 5/165;
(Continued)

(56) References Cited

U.S. PATENT DOCUMENTS 8,814,801 B2  8/2014 Tsuji et al.
2003/0036685 A1  2/2003 Goodman
(Continued)

FOREIGN PATENT DOCUMENTS

JP  2011-110206 A  6/2011
JP  2015-198740 A  11/2015
(Continued)

OTHER PUBLICATIONS

V Bhavana et al., "Feasibility of Authenticating Medical Data Using Photoplethysmography(ppg) as Signature Mark", vol. 4, Issue 1, ISSN: 2277 128X, Jan. 2014, pp. 635-641, 7 pages total.
(Continued)

*Primary Examiner* — Joseph M Dietrich
*Assistant Examiner* — Michael T. Holtzclaw
(74) *Attorney, Agent, or Firm* — Sughrue Mion, PLLC

(57) ABSTRACT

An apparatus for estimating bio-information includes: a sensor configured to obtain a bio-signal from an object; and a processor configured to obtain a second-order differential signal of the bio-signal, to detect at least one of an inflection point in a predetermined period of the second-order differential signal, and a zero-crossing point in the predetermined period of the second-order differential signal, to extract a feature based on the detected at least one of the inflection point and the zero-crossing point, and to estimate bio-information based on the extracted feature.

9 Claims, 12 Drawing Sheets

(51) Int. Cl.
  *A61B 5/02* (2006.01)
  *G16H 40/67* (2018.01)
  *A61B 5/0205* (2006.01)
  *A61B 5/021* (2006.01)
  *A61B 5/16* (2006.01)

(52) U.S. Cl.
  CPC .............. *G16H 50/30* (2018.01); *A61B 5/021* (2013.01); *A61B 5/02007* (2013.01); *A61B 5/165* (2013.01); *A61B 5/681* (2013.01); *A61B 5/6898* (2013.01)

(58) Field of Classification Search
  CPC ... A61B 5/681; A61B 5/6898; A61B 5/02416; A61B 5/02108; A61B 5/0002; A61B 5/0006; A61B 5/02438; A61B 5/6802; A61B 5/6803; A61B 5/746; A61B 5/0059; A61B 5/7275; A61B 5/7278; G16H 40/67; G16H 50/30; G16H 50/20
  See application file for complete search history.

(56) References Cited

U.S. PATENT DOCUMENTS

| | | | |
|---|---|---|---|
| 2007/0185400 A1 | 8/2007 | O'Rourke | |
| 2009/0043179 A1 | 2/2009 | Melker et al. | |
| 2009/0326386 A1 | 12/2009 | Sethi et al. | |
| 2011/0201950 A1 | 8/2011 | Poupko et al. | |
| 2013/0079647 A1 | 3/2013 | McGonigle et al. | |
| 2016/0135692 A1 | 5/2016 | Lisogurski et al. | |
| 2016/0270668 A1 | 9/2016 | Gil | |
| 2017/0000355 A1 | 1/2017 | Lenehan et al. | |
| 2017/0209055 A1 | 7/2017 | Pantelopoulos et al. | |
| 2019/0029538 A1 | 1/2019 | Jang | |
| 2019/0142286 A1 | 5/2019 | Mouradian | |
| 2019/0159682 A1 | 5/2019 | Nakajima et al. | |
| 2020/0121262 A1 | 4/2020 | De Haan | |

FOREIGN PATENT DOCUMENTS

| KR | 10-2002-0002450 A | 1/2002 |
|---|---|---|
| KR | 10-2011-0032107 A | 3/2011 |
| KR | 10-1503604 B1 | 3/2015 |
| KR | 10-2019-0011592 A | 2/2019 |
| WO | 2018/102486 A1 | 6/2018 |

OTHER PUBLICATIONS

Uldis Rubins, "Finger and ear photoplethysmogram waveform analysis by fitting with Gaussians", Medical & Biological Engineering, DOI: 10.1007/s11517-008-0406-z, Nov. 2008, 7 pages total.

Youngzoon Yoon et al., "Nonconstrained Blood Pressure Measurement by Photoplethysmography", Journal of the Optical Society of Korea, vol. 10, No. 2, Jun. 2006, pp. 91-95, 5 pages total.

Jayasree V.K et al., "Non-invasive Studies on Age Related Parameters Using a Blood Volume Pulse Sensor", Measurement Science Review, vol. 8, Section 2, No. 4, 10.2478/v10048-008-0020-0, 2008, pp. 82-86, 5 pages total.

Sandrine C. Millasseau et al., "The Vascular Impact of Aging and Vasoactive Drugs: Comparison of Two Digital vol. Pulse Measurements", American Journal of Hypertension, Ltd., doi: 10.1016/S0895-7061(03)00569-7, vol. 16, No. 6, Jun. 2003, pp. 467-472, 6 pages total.

Martin C Baruch et al., "Validation of the pulse decomposition analysis algorithm using central arterial blood pressure", BioMedical Engineering OnLine, 13:96, 2014, pp. 1-19, 19 pages total.

Communication dated Nov. 17, 2020, from the European Patent Office in counterpart European Application No. 20178507.8.

APPARATUS AND METHOD FOR ESTIMATING BIO-INFORMATION

CROSS-REFERENCE TO RELATED APPLICATION(S)

This application is a continuation application of U.S. application Ser. No. 16/874,843, filed May 15, 2020, which claims priority from Korean Patent Application No. 10-2019-0113041, filed on Sep. 11, 2019, in the Korean Intellectual Property Office, the entire disclosure of which is incorporated herein by reference for all purposes.

BACKGROUND

1. Field

Apparatuses and methods consistent with example embodiments relate to non-invasively estimating bio-information.

2. Description of Related Art

Recently, with the aging population, rising medical costs, and a lack of medical personnel for specialized medical services, research is being actively conducted on information technology (IT)-medical convergence technologies, in which IT technology and medical technology are combined. Particularly, monitoring of the health condition of a human body is not limited to medical institutions, but is expanding to mobile healthcare fields that may monitor a user's health condition anywhere and anytime in daily life such as at home or office. Examples of bio-signals, which indicate the health condition of individuals, include an electrocardiography (ECG) signal, a photoplethysmogram (PPG) signal, an electromyography (EMG) signal, and the like, and various bio-signal sensors have been developed to measure these signals in daily life. Particularly, a PPG sensor may estimate blood pressure of a human body by analyzing a shape of pulse waves which reflect cardiovascular status and the like.

According to studies on the PPG signal, the entire PPG signal is a superposition of propagation waves departing from the heart and moving toward the distal portions of the body, and reflection waves returning from the distal portions. Further, it has been known that information for estimating blood pressure may be obtained by extracting various features associated with the propagation waves or the reflection waves.

SUMMARY

In accordance with an aspect of an example embodiment, there is provided an apparatus for estimating bio-information, including: a sensor configured to obtain a bio-signal from an object; and a processor configured to obtain a second-order differential signal of the bio-signal, to detect at least one of an inflection point in a predetermined period of the second-order differential signal, and a zero-crossing point in the predetermined period of the second-order differential signal, to extract a feature based on the detected at least one of the inflection point and the zero-crossing point, and to estimate bio-information based on the extracted feature.

The sensor may include a pulse wave sensor, including a light source configured to emit light onto the object, and a detector configured to detect the light emitted onto the object and reflected or scattered from the object.

The predetermined period may include a time interval between a first local maximum point and a first local minimum point of the second-order differential signal.

The inflection point may be a point, at which a waveform of the second-order differential signal changes from being concave downward to being convex upward with respect to a time axis of the second-order differential signal.

The processor may be further configured to obtain a fourth-order differential signal of the bio-signal, detect a first time point in a predetermined period of the fourth-order differential signal, an amplitude at the first time point in the fourth-order differential signal being greater than zero and an amplitude at a second time point after the first time point being less than zero, and detect a point of the second-order differential signal, which corresponds to the first time point, as the inflection point.

Based on a determination that the inflection point is not detected in the predetermined period of the second-order differential signal, the processor may be further configured to determine whether the zero-crossing point is present in the predetermined period of the second-order differential signal based on at least one predetermined criterion.

The at least one predetermined criterion may include at least one of: a first criterion as to whether a first value, obtained by subtracting a time corresponding to a first local maximum point of the second-order differential signal from a time corresponding to a first local minimum point of the second-order differential signal, is greater than a first threshold; and a second criterion as to whether the first value is greater than a value, obtained by multiplying a second value with a second threshold, the second value being obtained by subtracting the time corresponding to the first local minimum point from a time corresponding to a second local maximum point of the second-order differential signal.

Based on a determination that the zero-crossing point is present in the predetermined period of the second-order differential signal, the processor may be further configured to obtain a first-order differential signal of the bio-signal, and detect a time point, at which an amplitude of the first-order differential signal is maximum, as the zero-crossing point.

Based on a determination that the zero-crossing point is not present in the predetermined period of the second-order differential signal, the processor may be further configured to detect a local minimum point in the predetermined period of the second-order differential signal, and extract the feature based on the detected local minimum point.

The processor may be further configured to detect a local minimum point in the predetermined period of the second-order differential signal, and based on a determination that the local minimum point is not detected in the predetermined period of the second-order differential signal, the processor is further configured to detect the inflection point in the predetermined period of the second-order differential signal.

The processor may be further configured to extract an amplitude of the bio-signal, which corresponds to the inflection point, as the feature.

The processor may be further configured to extract, as the feature, an amplitude of the bio-signal which corresponds to at least one of the zero-crossing point, an internally dividing point between the zero-crossing point and a start point of the predetermined period, and an internally dividing point between the zero-crossing point and an end point of the predetermined period.

The bio-information may include an at least one of a blood pressure, a vascular age, an arterial stiffness, an aortic pressure waveform, a stress index, and a degree of fatigue.

In accordance with an aspect of an example embodiment, there is provided a method of estimating bio-information, including: obtaining a bio-signal from an object; obtaining a second-order differential signal of the bio-signal; detecting at least one of an inflection point in a predetermined period of the second-order differential signal and a zero-crossing point in the predetermined period of the second-order differential signal; extracting a feature based on the detected at least one of the inflection point and the zero-crossing point; and estimating bio-information based on the extracted feature.

The predetermined period may include a time interval between a first local maximum point and a first local minimum point of the second-order differential signal.

The inflection point may be a point, at which a waveform of the second-order differential signal changes from being concave downward to being convex upward with respect to a time axis of the second-order differential signal.

The detecting may include: obtaining a fourth-order differential signal of the bio-signal; detecting a first time point in a predetermined period of the fourth-order differential signal, an amplitude at the first time point in the fourth-order differential signal being greater than zero and an amplitude at a second time point after the first time point being less than zero; and detecting a point of the second-order differential signal, which corresponds to the first time point, as the inflection point.

The detecting may include, based on a determination that the inflection point is not detected in the predetermined period of the second-order differential signal, determining whether the zero-crossing point is present in the predetermined period of the second-order differential signal based on at least one predetermined criterion.

The at least one predetermined criterion may include at least one of: a first criterion as to whether a first value, obtained by subtracting a time corresponding to a first local maximum point of the second-order differential signal from a time corresponding to a first local minimum point of the second-order differential signal, is greater than a first threshold; and a second criterion as to whether the first value is greater than a value, obtained by multiplying a second value with a second threshold, the second value being obtained by subtracting the time corresponding to the first local minimum point from a time corresponding to a second local maximum point of the second-order differential signal.

The detecting may include, based on a determination that the zero-crossing point is present in the predetermined period of the second-order differential signal, obtaining a first-order differential signal of the bio-signal, and detecting a time point, at which an amplitude of the first-order differential signal is maximum, as the zero-crossing point.

The method may further include, based on a determination that the zero-crossing point is not present in the predetermined period of the second-order differential signal, detecting a local minimum point in the predetermined period of the second-order differential signal, wherein the extracting includes extracting the feature based on the detected local minimum point.

The method may further include detecting a local minimum point in the predetermined period of the second-order differential signal, and based on a determination that the local minimum point is not detected in the predetermined period of the second-order differential signal, detecting the inflection point in the predetermined period of the second-order differential signal.

The extracting may include extracting an amplitude of the bio-signal, which corresponds to the inflection point, as the feature.

The extracting may include extracting, as the feature, an amplitude of the bio-signal which corresponds to at least one of the zero-crossing point, an internally dividing point between the zero-crossing point and a start point of the predetermined period, and an internally dividing point between the zero-crossing point and an end point of the predetermined period.

The bio-information may include at least one of a blood pressure, a vascular age, an arterial stiffness, an aortic pressure waveform, a stress index, and a degree of fatigue.

In accordance with an aspect of an example embodiment, there is provided an apparatus for estimating bio-information, including: a sensor configured to obtain a bio-signal from an object; and a processor configured to obtain a second-order differential signal of the bio-signal, to detect, as a characteristic point, at least one of a local minimum point, an inflection point, and a zero-crossing point in a predetermined period of the second-order differential signal, to extract a feature based on the detected characteristic point, and to estimate bio-information based on the extracted feature.

The processor may be further configured to detect, as the inflection point, a point at which a waveform of the second-order differential signal changes from being concave downward to being convex upward in the predetermined period.

Based on a determination that the inflection point is not detected in the predetermined period, the processor may be further configured to detect the characteristic point from the local minimum point and the zero-crossing point in the predetermined period, the predetermined period being a time interval between a first local maximum point and a first local minimum point of the second-order differential signal.

The processor may be further configured to determine whether to detect the local minimum point or the zero-crossing point based on a time of the first local minimum point and a time of a second local maximum point.

BRIEF DESCRIPTION OF THE DRAWINGS

The above and/or other aspects of the disclosure will become apparent and more readily appreciated from the following description of the example embodiments, taken in conjunction with the accompanying drawings, in which.

DETAILED DESCRIPTION

Figure 1:
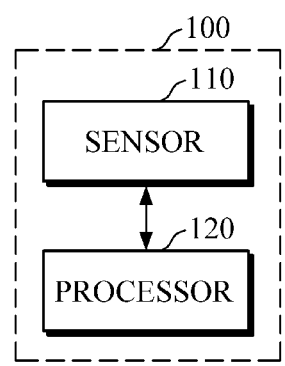
FIG. 1 is a block diagram illustrating an apparatus for estimating bio-information according to an example embodiment.

Example embodiments are described in greater detail below with reference to the accompanying drawings.

In the following description, like drawing reference numerals are used for like elements, even in different drawings. The matters defined in the description, such as detailed construction and elements, are provided to assist in a comprehensive understanding of the example embodiments. However, it is apparent that the example embodiments can be practiced without those specifically defined matters. Also, well-known functions or constructions are not described in detail since they would obscure the description with unnecessary detail. The relative size and depiction of the elements may be exaggerated for clarity, illustration, and convenience.

It will be understood that, although the terms first, second, etc. may be used herein to describe various elements, these elements should not be limited by these terms. These terms are only used to distinguish one element from another. Any references to singular may include plural unless expressly stated otherwise. In addition, unless explicitly described to the contrary, an expression such as "comprising" or "including" will be understood to imply the inclusion of stated elements but not the exclusion of any other elements. Also, the terms, such as 'part' or 'module', etc., should be understood as a unit that performs at least one function or operation and that may be embodied as hardware, software, or a combination thereof.

Expressions such as "at least one of," when preceding a list of elements, modify the entire list of elements and do not modify the individual elements of the list. For example, the expression, "at least one of a, b, and c," should be understood as including only a, only b, only c, both a and b, both a and c, both b and c, all of a, b, and c, or any variations of the aforementioned examples.

Hereinafter, example embodiments of an apparatus and a method for estimating bio-information will be described in detail with reference to the accompanying drawings.

FIG. 1 is a block diagram illustrating an apparatus for estimating bio-information according to an example embodiment. The apparatus 100 for estimating bio-information may be embedded in a terminal, such as a smartphone, a tablet personal computer (PC), a desktop computer, a laptop computer, and the like, or may be manufactured as an independent hardware device. In a case where the apparatus 100 for estimating bio-information is manufactured as an independent hardware device, the device may be a wearable device to be worn on an object of a user to allow the user to easily measure bio-information while carrying the device. Examples of the wearable device may include a wristwatch-type wearable device, a bracelet-type wearable device, a wristband-type wearable device, a ring-type wearable device, a glasses-type wearable device, a headband-type wearable device, or the like, but the wearable device is not limited thereto, and may be modified for various purposes, such as a fixed type device and the like used in medical institutions for measuring and analyzing bio-information.

Referring to FIG. 1, the apparatus 100 for estimating bio-information includes a sensor 110 and a processor 120.

As illustrated in FIG. 1, the sensor 110 may obtain a bio-signal from an object, and may transmit the obtained bio-signal to the processor 120. The bio-signal may include a Photoplethysmogram (PPG) signal (hereinafter referred to as a "pulse wave signal"). However, the bio-signal is not limited thereto, and may include various bio-signals, such as an electrocardiography (ECG) signal, a photoplethysmogram (PPG) signal, an electromyography (EMG) signal, and the like, which may be modeled by a sum of a plurality of waveform components.

For example, the sensor 110 may include a PPG sensor for measuring the PPG signal. The PPG sensor may include a light source for emitting light onto the object and a detector for measuring the PPG signal by detecting light that is emitted by the light source and scattered or reflected from body tissue of the object. The light source may include at least one of a light emitting diode (LED), a laser diode (LD), and a phosphor, but is not limited thereto. The detector may include a photo diode.

Upon receiving a control signal from the processor 120, the PPG sensor of the sensor 110 obtain a pulse wave signal from the object. The object may be a body part which comes into contact with or is adjacent to the PPG sensor, and may be a body part where pulse waves may be easily measured using photoplethysmography. For example, the object may be an area on the wrist that is adjacent to the radial artery, or an upper portion of the wrist where veins or capillaries are located. There may be external factors such as a thickness of skin tissue in the wrist and the like, which may cause errors in measurement of the pulse waves. In a case where the pulse waves are measured on an area of skin where the radial artery passes, measurement may be relatively less affected by the external factors. However, the skin area is not limited thereto, and may be any distal portions of the body, such as fingers, toes, and the like where blood vessels are densely located.

Upon receiving a request for estimating bio-information from a user, the processor 120 may generate a control signal for controlling the sensor 110, and may transmit the control signal to the sensor 110. Further, the processor 120 may receive a bio-signal from the sensor 110 and may estimate bio-information by analyzing the received bio-signal. The bio-information may include a blood pressure, a vascular age, an arterial stiffness, an aortic pressure waveform, a stress index, a degree of fatigue, and the like, but is not limited thereto.

Upon receiving the bio-signal from the sensor 110, the processor 120 may perform preprocessing, such as filtering for removing noise, amplifying the bio-signal, converting the signal into a digital signal, and the like.

The processor 120 may extract features, which are usable for estimating bio-information, by analyzing a waveform of the received bio-signal, and may estimate bio-information by using the extracted features. The processor 120 may detect a characteristic point based on a shape of the waveform of the bio-signal during a systolic phase, and may obtain features, related to a first pulse waveform component of the bio-signal, by using the detected characteristic point. For example, the processor 120 may obtain a second-order differential signal of the bio-signal, may detect at least one of a local minimum point, an inflection point, and a zero-crossing point as a characteristic point according to a shape of a waveform in a predetermined phase of the second-order differential signal, and may obtain features, related to the first pulse waveform component, by using the detected characteristic point.

Figure 2:
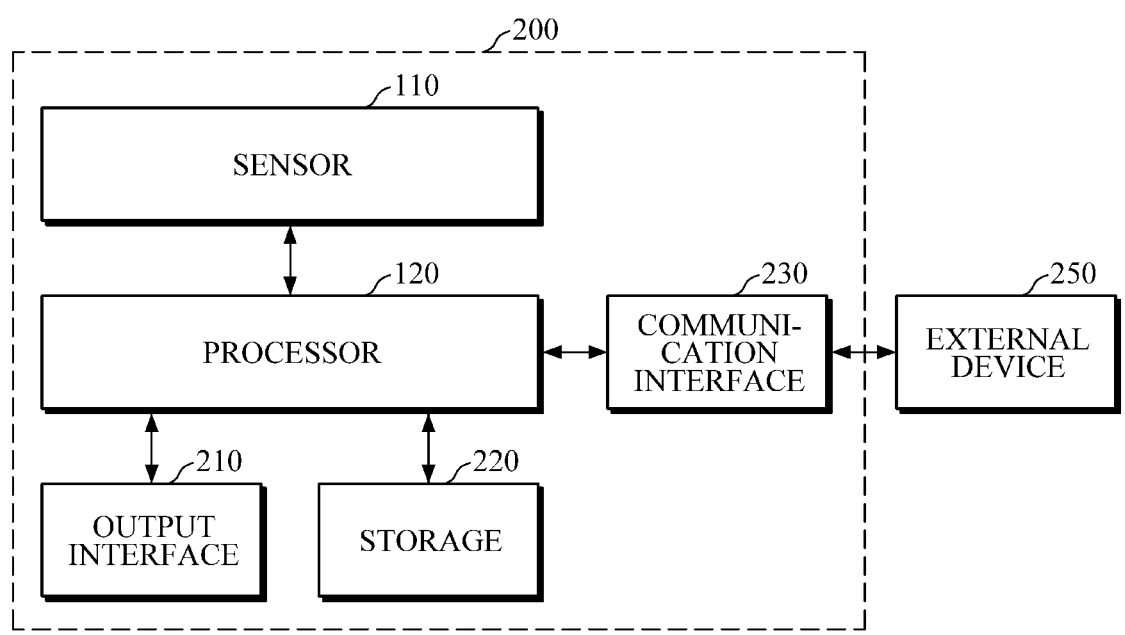
FIG. 2 is a block diagram illustrating an apparatus for estimating bio-information according to another example embodiment.

FIG. 2 is a block diagram illustrating an apparatus for estimating bio-information according to another example embodiment.

Referring to FIG. 2, the apparatus 200 for estimating bio-information includes a sensor 110, a processor 120, an output interface 210, a storage 220, and a communication interface 230.

The sensor 110 may measure a bio-signal from an object, and the processor 120 may estimate bio-information by using the bio-signal measured by the sensor 110.

The output interface 210 may output bio-signal information, measured by the sensor 110, and processing results of the processor 120, and may provide related information. The output interface 210 may provide the related information by using one or more of various visual and/or non-visual methods based on a display module (e.g., a display), a speaker, a haptic device (e.g., a vibrator), and the like which are mounted in the apparatus 200 for estimating bio-information.

For example, in a case where a blood pressure of a user is estimated, the output interface 210 may output the estimated blood pressure by using one or more of various visual methods, such as by changing a color, a line thickness, font, and the like based on whether the estimated blood pressure value falls within or outside a normal range. Additionally and/or alternatively, the output interface 210 may use one or more non-visual methods to output the estimated blood pressure by, for example, using an acoustic method such as using a voice, or output the estimated blood pressure by using a haptic method such as vibrations and/or tactile sensations and the like according to abnormal blood pressure levels being estimated. In addition, upon comparing the measured blood pressure with a previous measurement history, if it is determined that the measured blood pressure is abnormal, the output interface 210 may output related information (e.g., warning information) to the user, or may provide information to guide a user's action such as food information that the user should be careful about, information for booking a hospital appointment, and the like.

The storage 220 may store a variety of reference information to be used for estimating bio-information, the obtained bio-signal, the detected characteristic point, the extracted features, a bio-information estimation result, and the like. The variety of reference information to be used for estimating bio-information may include user information, such as a user's age, sex, occupation, current health condition, and the like, information on a bio-information estimation model, and the like, but the reference information is not limited thereto. The storage 230 may include at least one storage medium of a flash memory type memory, a hard disk type memory, a multimedia card micro type memory, a card type memory (e.g., a secure digital (SD) memory, an extreme Digital (XD) memory, etc.), a random access memory (RAM), a static random access memory (SRAM), a read only memory (ROM), an electrically erasable programmable read only memory (EEPROM), a programmable read only memory (PROM), a magnetic memory, a magnetic disk, and an optical disk, and the like, but is not limited thereto.

Upon receiving a control signal, including connection information of an external device 250, from the processor 120, the communication interface 230 may access a communication network using communication techniques to be connected with the external device 250. Upon connection with the external device 250, the communication interface 230 may receive a variety of information related to estimating bio-information from the external device 250, and may transmit the bio-signal measured by the sensor 110, the bio-information estimated by the processor 120, and the like to the external device 250. Examples of the external device 250 may include another apparatus for estimating bio-information, a cuff manometer for measuring cuff blood pressure and the like, a smartphone, a tablet PC, a desktop computer, a laptop computer, and the like, but the external device 250 is not limited thereto.

Examples of the communication techniques may include Bluetooth communication, Bluetooth low energy (BLE) communication, near field communication (NFC), wireless local area network (WLAN) communication, Zigbee communication, infrared data association (IrDA) communication, wireless fidelity (Wi-Fi) Direct (WFD) communication, Ultra-Wideband (UWB) communication, Ant+ communication, Wi-Fi communication, and mobile communication. However, these are merely examples and the disclosure is not intended to be limiting.

Figure 3:
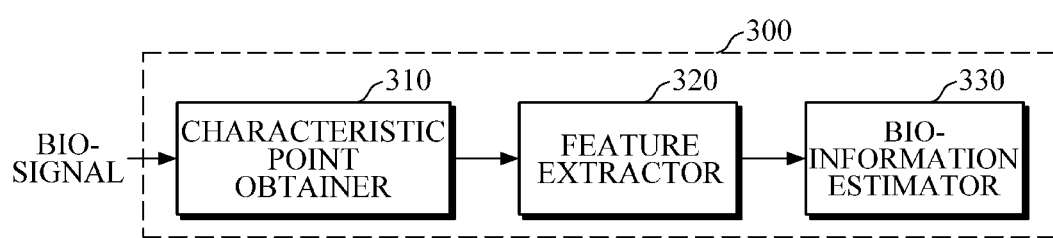
FIG. 3 is a block diagram illustrating a processor included in an apparatus for estimating bio-information according to an example embodiment.

FIG. 3 is a block diagram illustrating a processor included in an apparatus for estimating bio-information according to an example embodiment. FIGS. 4A, 4B, 4C, 4D, and 4E are diagrams explaining an example of extracting characteristic points from a bio-signal according to example embodiments. For example, a processor 300 illustrated in FIG. 3 may be included in any one of the apparatus 100 and the apparatus 200 according to the example embodiments of FIGS. 1 and 2.

Referring to FIG. 3, the processor 300 includes a characteristic point obtainer 310, a feature extractor 320, and a bio-information estimator 330.

The characteristic point obtainer 310 may extract a characteristic point by using a bio-signal obtained from an object. For example, the characteristic point obtainer 310 may obtain a second-order differential signal by performing second-order differentiation on the bio-signal, may detect pulse waveform components constituting a waveform of the bio-signal by analyzing a waveform of the obtained second-order differential signal, and obtain a characteristic point based on the detected pulse waveform components.

Figure 4A:
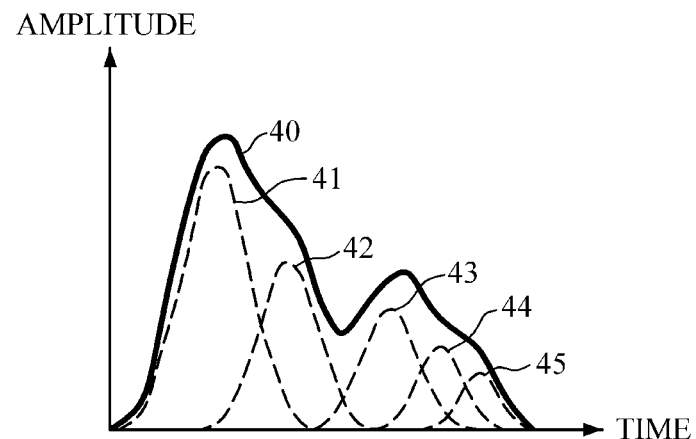
FIGS. 4A, 4B, 4C, 4D, and 4E are diagrams explaining an example of extracting characteristic points from a bio-signal according to example embodiments.

FIG. 4A is a diagram illustrating a waveform of a pulse wave signal 40 which is constituted by a superposition of five constituent pulses 41, 42, 43, 44, and 45. The characteristic point obtainer 310 may extract information such as time and/or amplitude information and the like at points associated with each of the constituent pulses 41, 42, 43, 44, and 45, as characteristic points, and may extract features, having a high correlation with a blood pressure, based on the extracted characteristic points. Generally, a first constituent pulse through a third constituent pulse are mainly used to estimate a blood pressure. Pulses after the third constituent pulse may not be detected depending on individuals or due to noise or have a low correlation with a blood pressure.

Figure 4B:
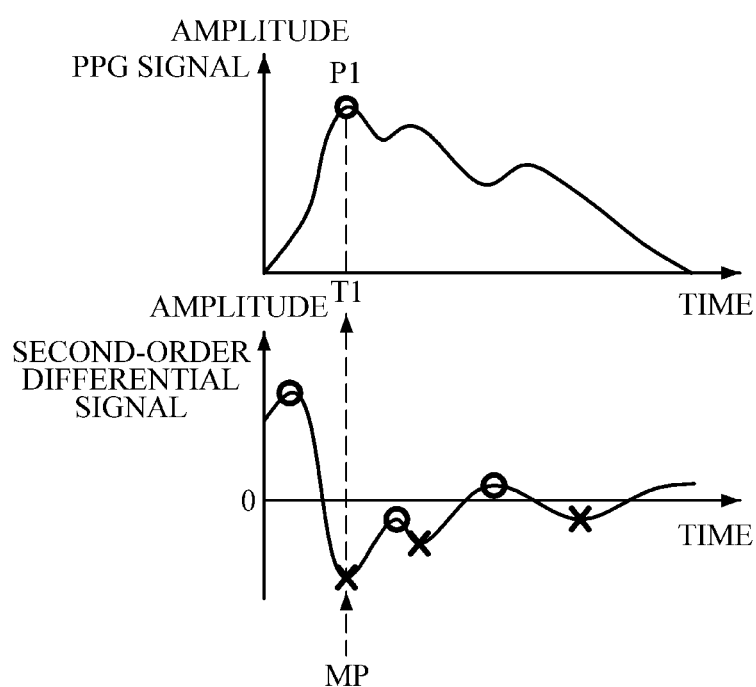
Figure 4C:
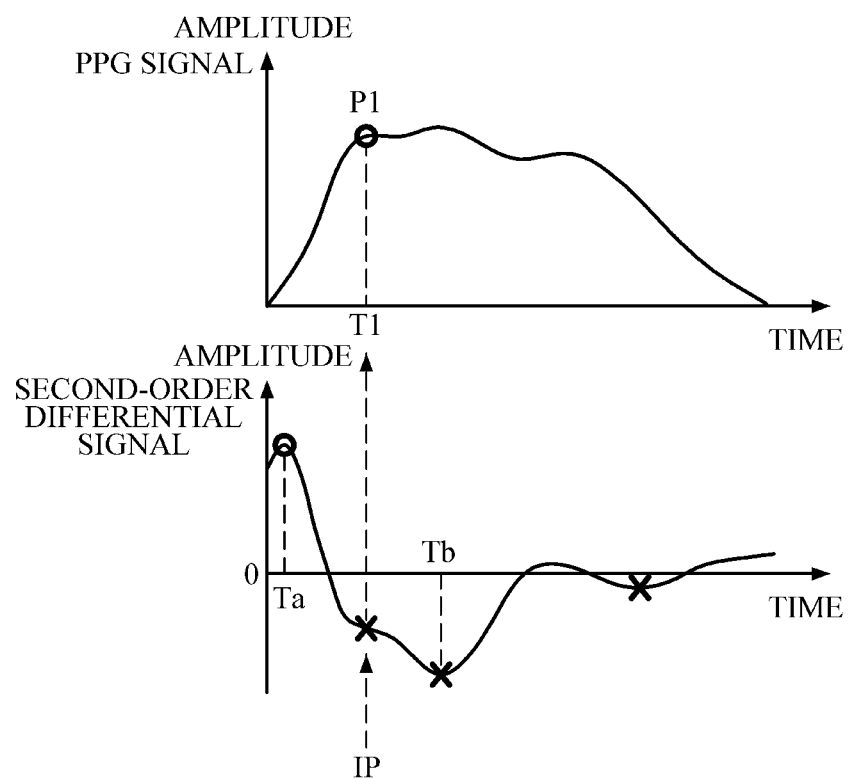
Figure 4D:
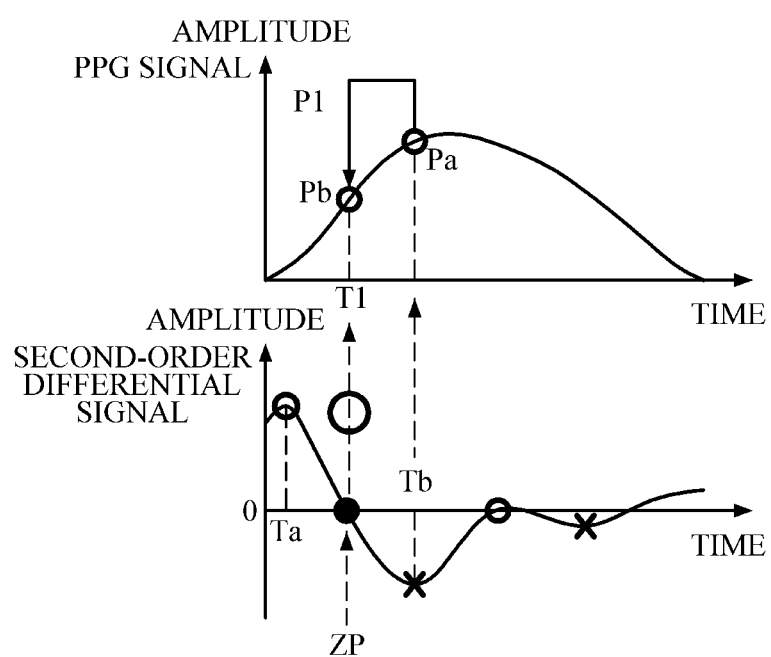

FIGS. 4B, 4C, and 4D are diagrams illustrating an example of detecting points, associated with constituent pulses, as characteristic points by using a second-order differential signal of a bio-signal according to example embodiments.

Referring to FIG. 4B, upon obtaining a PPG signal, as shown in an upper view of FIG. 4B, the characteristic point obtainer 310 may obtain a second-order differential signal, as shown in a lower view of FIG. 4B, by performing second-order differentiation of the obtained PPG signal. Further, the characteristic point obtainer 310 may detect a first local minimum point in a systolic phase of the obtained second differential signal, and may obtain the detected first local minimum point MP as a characteristic point associated with the first pulse waveform component. In this case, the characteristic point obtainer 310 may determine whether a local minimum point of the second-order differential signal is normally present in the systolic phase. For example, the characteristic point obtainer 310 may determine whether a local minimum point exists in an interval which is obtained by dividing a one-period interval of the entire PPG signal at a predetermined ratio (e.g., ⅕), but is not limited thereto.

As described above, upon detecting the first local minimum point from the second-order differential signal as a characteristic point associated with the first pulse waveform component, the feature extractor 320 may extract an amplitude P1 of the PPG signal, which corresponds to a time T1 of the detected local minimum point, as a feature associated with the first pulse waveform component.

However, in the case where a bio-signal is measured from a contact surface of the human body, which is adjacent to capillaries rather than arteries, high frequency components disappear and only low frequency components remain, thereby producing a smooth waveform of the bio-signal. In this case, information on the first pulse waveform component, mainly having high frequency waveform components in the systolic phase, e.g., propagation waves, is generally lost, such that it may be difficult to stably extract the first pulse waveform component. Accordingly, if non-ideal waveform shapes are detected for various reasons such as due to noise, a non-ideal contact state of the human body, an unusual vascular structure of a subject, and the like, the characteristic point extractor 320 may obtain characteristic points, associated with the first pulse waveform component, by detecting an inflection point or a zero-crossing point in a predetermined period of the second-order differential signal, which will be described below with reference to FIGS. 4C and 4D.

FIG. 4C is a diagram illustrating an example in which a waveform of the PPG signal, as shown in an upper view of FIG. 4C, has a smoother shape compared to FIG. 4B due to various factors. In the PPG signal, a local minimum point, associated with the first pulse waveform component, may not clearly appear in the systolic phase of the second-order differential signal, as shown in a lower view of FIG. 4C. In the case where there is no local minimum point in the systolic phase of the second-order differential signal, the characteristic point obtainer 310 may obtain a characteristic point by detecting an inflection point IP in a predetermined period of the second-order differential signal. In the example shown in the lower view of FIG. 4C, the inflection point IP is a point at which a waveform of the second-order differential signal changes from being concave "downward" to convex "upward" during the systolic phase; and the predetermined period may be a time interval between a time Ta corresponding to a first local maximum point and a time Tb corresponding to a first local minimum point. By considering an apparatus performance and the like, an interval between a random start point (e.g., $T_{start}=Ta+(\tfrac{2}{5})*(Tb-Ta)$) and a random end point (e.g., $T_{end}=T_b$) of the predetermined period may be set as a detection interval for more rapid detection of the inflection point IP.

For example, the characteristic point obtainer 310 may obtain a fourth-order differential signal by performing fourth order differentiation on the bio-signal. The characteristic point obtainer 310 may detect a first time t which satisfies a condition that an amplitude of the fourth-order differential signal at the first time t is greater than zero, and an amplitude of the fourth-order differential signal at a second time t+1 after the first time t is less than zero. Upon detecting the first time t, which satisfies the condition, the characteristic point obtainer 310 may detect a point of the second-order differential signal, corresponding to the first time t, as an inflection point IP.

When the characteristic point obtainer 310 detects the inflection point IP, the feature extractor 320 may extract an amplitude P1, corresponding to the time of the inflection point IP, as a feature from the PPG signal.

In another example, referring to FIG. 4D, in the case where a PPG signal is measured from a contact surface of the human body, which is adjacent to capillaries rather than arteries, only low frequency components remain in the waveform of the PPG signal, as can be seen from an upper view of FIG. 4D, such that the waveform may have a more smoother shape at a point Pb which is associated with the first pulse waveform component. In this case, an inflection point may not be detected at the point, associated with the first pulse waveform component, in the second-order differential signal, as shown in a lower view of FIG. 4D.

That is, in the case where the waveform of the PPG signal has a very smooth shape at the point Pb which is associated with the first pulse waveform component, a position corresponding to the local minimum point or the inflection point may converge on a zero-crossing point ZP. In this case, the characteristic point obtainer 310 may detect the zero-crossing point ZP from a predetermined period of the second-order differential signal, as shown in the lower view of FIG. 4D, and may obtain a characteristic point based on the zero-crossing point ZP. In this case, the predetermined period may refer to a time interval between the time Ta of the first local maximum point and the time Tb of the first local minimum point of the second-order differential signal, as described above.

For example, the characteristic point obtainer 310 may detect the zero-crossing point ZP by detecting a point where an amplitude of the second-order differential signal is zero in the predetermined period, or by obtaining a first-order differential signal of the bio-signal and detecting a point where an amplitude of the first-order differential signal is maximum in the predetermined period.

When the zero-crossing point ZP is obtained as a characteristic point, the feature extractor 320 may obtain an amplitude P1 of the PPG signal, which corresponds to the time T1 of the zero-crossing point ZP, as a feature.

In a case where a local minimum point or an inflection point does not clearly appear in the predetermined period between the time Ta and the time Tb of the second-order differential signal, if the first local minimum point (or a point corresponding to Tb of FIG. 4D) is obtained as a characteristic point associated with the first pulse waveform, an amplitude value Pa may be erroneously extracted from the PPG signal, thereby reducing accuracy in estimating bio-information.

To solve this problem, according to an example embodiment, if there is no inflection point detected in a predetermined period of the second-order differential signal, the characteristic point obtainer 310 may first determine whether a local minimum point or a zero-crossing point is detected from the waveform of the PPG signal. If a predetermined criterion is satisfied, the characteristic point obtainer 310 may determine that a zero-crossing point is detected in the predetermined period of the second-order differential signal.

Figure 4E:
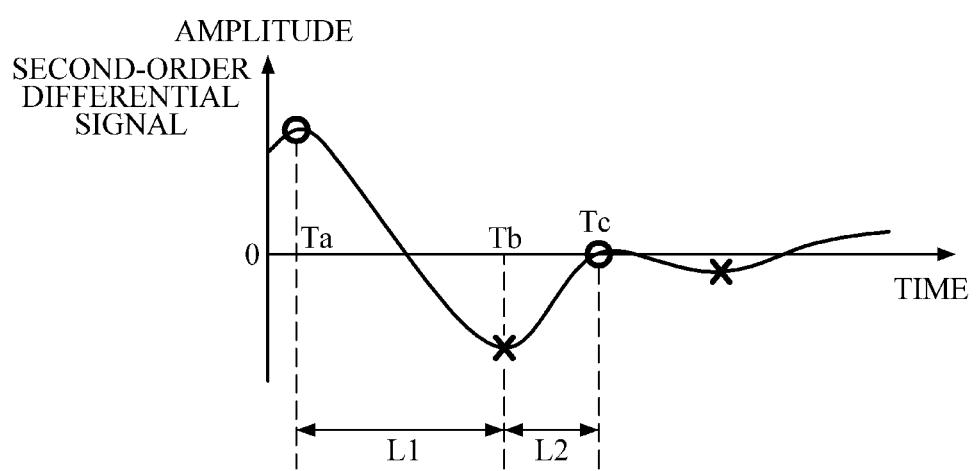

For example, referring to FIG. 4E, the predetermined criterion may be preset based on a first value L1, obtained by subtracting a time Ta of the first local maximum point from a time Tb of the first local minimum point, and/or a second value L2 obtained by subtracting the time Tb of the first local minimum point from a time Tc of a second local maximum point. For example, a first criterion may be preset such that the first value L1 is greater than a first threshold, or a second criterion may be preset such that the first value L1 is greater than a predetermined ratio of the second value L2, e.g., if the first value L1 is greater than a value obtained by multiplying the second value L2 by a second threshold, the characteristic point obtainer 310 may determine that there is a zero-crossing point. However, the criterion is not limited thereto, and the characteristic point obtainer 310 may determine that there is a zero-crossing point if any one of the first and second criteria is satisfied or if both the criteria are satisfied.

In an example embodiment, upon receiving the bio-signal from the sensor 110, the characteristic point obtainer 310 may obtain a second-order differential signal of the bio-signal, detect an inflection point in a predetermined period of the second-order differential signal, and obtain the inflection point as a characteristic point. If there is no inflection point detected in the predetermined period, the characteristic point obtainer 310 may detect a zero-crossing point, and obtain the detected zero-crossing point as the characteristic point. If it is determined that there is no zero-crossing point detected in the predetermined period, the characteristic point obtainer 310 may obtain a local minimum point as the characteristic point.

In another example embodiment, the characteristic point obtainer 310 may detect a local minimum point in a predetermined period of the second-order differential signal, and obtain the detected local minimum point as the characteristic point. If there is no local minimum point detected in the predetermined period, the characteristic point obtainer 310 may detect an inflection point and obtain the detected inflection point as the characteristic point. If there is no inflection point detected in the predetermined period, the characteristic point obtainer 310 may detect a zero-crossing point and obtain the zero-crossing point as the characteristic point. A detection order of characteristic points may be predetermined based on various conditions, such as computing performance of an apparatus for estimating bio-information, a bio-signal measurement portion, a user's health condition, a measured temperature and humidity, and the like.

Further, in addition to the characteristic points associated with the first constituent pulse, e.g., propagation waves, the characteristic point obtainer 310 may further obtain pulse waveform components associated with second and third constituent pulses, e.g., reflection waves, and/or other various points, as characteristic points by using various methods as described above. The feature extractor 320 may obtain features based on one of or a combination of times of the characteristic points and/or one or more amplitudes of the bio-signal corresponding to the one of or a combination of times of the characteristic points.

When the feature extractor 320 extracts features, the bio-information estimator 330 may estimate bio-information by using the extracted features. The bio-information estimator 330 may estimate bio-information based on the extracted features by applying a predetermined bio-information estimation model.

Figure 5:
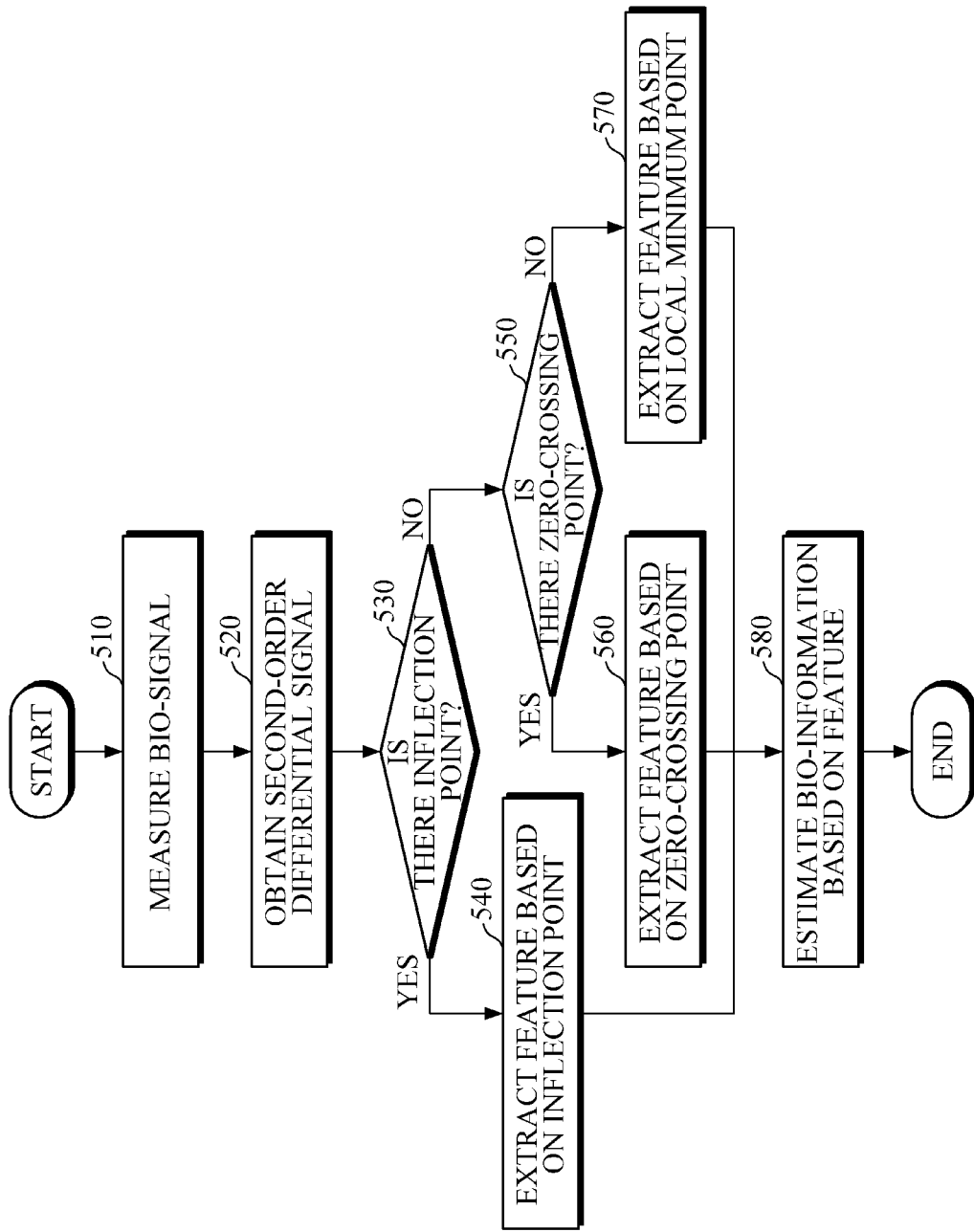
FIG. 5 is a flowchart illustrating a method of estimating bio-information according to an example embodiment.

FIG. 5 is a flowchart illustrating a method of estimating bio-information according to an example embodiment.

The method of FIG. 5 is an example of a method of estimating bio-information according to an example embodiment. The method of FIG. 5 may be performed by any one of the apparatuses 100 and 200 for estimating bio-information according to the example embodiments of FIGS. 1 and 2.

Upon receiving a request for estimating bio-information, an apparatus (e.g., the apparatus 100 or 200) for estimating bio-information according to an example embodiment may measure a bio-signal from an object in 510.

The apparatus for estimating bio-information according to an example embodiment may provide an interface for various interactions with a user, and may receive the request for estimating bio-information from the user through the provided interface. Alternatively, the apparatus for estimating bio-information according to an example embodiment may receive a request for estimating bio-information from an external device. In this case, the request for estimating bio-information of the external device may include a request for providing a bio-information estimation result. In the case where the external device includes a bio-information estimation algorithm, the request for estimating bio-information may include a request for providing information on characteristic points or features. The external device may be a smartphone, a tablet PC, a mobile device, and the like.

The apparatus for estimating bio-information according to an example embodiment may obtain a second-order differential signal by performing second-order differentiation on the measured bio-signal in 520.

The apparatus for estimating bio-information according to an example embodiment may detect an inflection point in a predetermined period of the second-order differential signal in 530. The predetermined period may be a time interval between a time of a first local maximum point and a time of a first local minimum point on a time axis of the second-order differential signal; and the inflection point may be a point at which a waveform of the second-order differential signal changes from being concave "downward" to convex "upward" with a lapse of time in the predetermined period.

Upon detecting the inflection point in 530, the apparatus for estimating bio-information according to an example embodiment may extract a feature based on the detected inflection point in 540. For example, the apparatus for estimating bio-information according to an example embodiment may extract an amplitude of the bio-signal, at a time corresponding to a time of the inflection point in the second-order differential signal, as a feature. As described above, if an amplitude at a specific time in a predetermined period of a fourth-order differential signal of the bio-signal is greater than zero, and an amplitude at a subsequent time in the predetermined period of the fourth-order differential signal of the bio-signal is less than zero, the apparatus for estimating bio-information according to an example embodiment may detect a point, corresponding to the specific time, as an inflection point in the second-order differential signal.

On the other hand, if there is no inflection point detected in 530, the apparatus for estimating bio-information according to an example embodiment may determine whether there is a zero-crossing point in a predetermined period of the second-order differential signal in 550. For example, if a predetermined criterion is satisfied based on at least one of a time difference between the first local maximum point and the first local minimum point of the second-order differential signal and/or a time difference between the first local minimum point and the second local maximum point, the apparatus for estimating bio-information according to an example embodiment may determine that there is a zero-crossing point.

Upon determining that there is a zero-crossing point in the predetermined period of the second-order differential signal, the apparatus for estimating bio-information according to an example embodiment may extract a feature based on the zero-crossing point in 560. For example, the apparatus for estimating bio-information according to an example embodiment may detect a specific time, at which an amplitude in a predetermined period of the second-order differential signal becomes zero, and may extract an amplitude in the bio-signal, corresponding to the detected specific time, as a feature.

On the other hand, if it is determined that there is no zero-crossing point in 550, the apparatus for estimating bio-information according to an example embodiment may extract a feature based on a local minimum point in a predetermined period of the second-order differential signal in 570. For example, the apparatus for estimating bio-information according to an example embodiment may detect a local minimum point in a predetermined period of the second-order differential signal, and may extract an amplitude in the bio-signal, corresponding to a time of the local minimum point, as a feature.

Next, the apparatus for estimating bio-information according to an example embodiment may estimate bio-information in 580 based on the features extracted in 540, 560, or 570. In this case, a bio-information estimation model may be pre-generated. The bio-information estimation model may be based on a linear and/or non-linear function(s). In addition to the extracted features, the apparatus for estimating bio-information according to an example embodiment may extract additional features, and may estimate bio-information by applying the bio-information estimation model to the extracted features. Further, upon estimating bio-information, the apparatus for estimating bio-information according to an example embodiment may provide a bio-information estimation result to a user. For example, the apparatus for estimating bio-information according to an example embodiment may provide the estimated bio-information for the user by using various visual and/or non-visual methods. In addition, the apparatus for estimating bio-information according to an example embodiment may determine the user's health condition based on the estimated bio-information, and may warn the user or may provide a response action for the user based on the determination.

Figure 6:
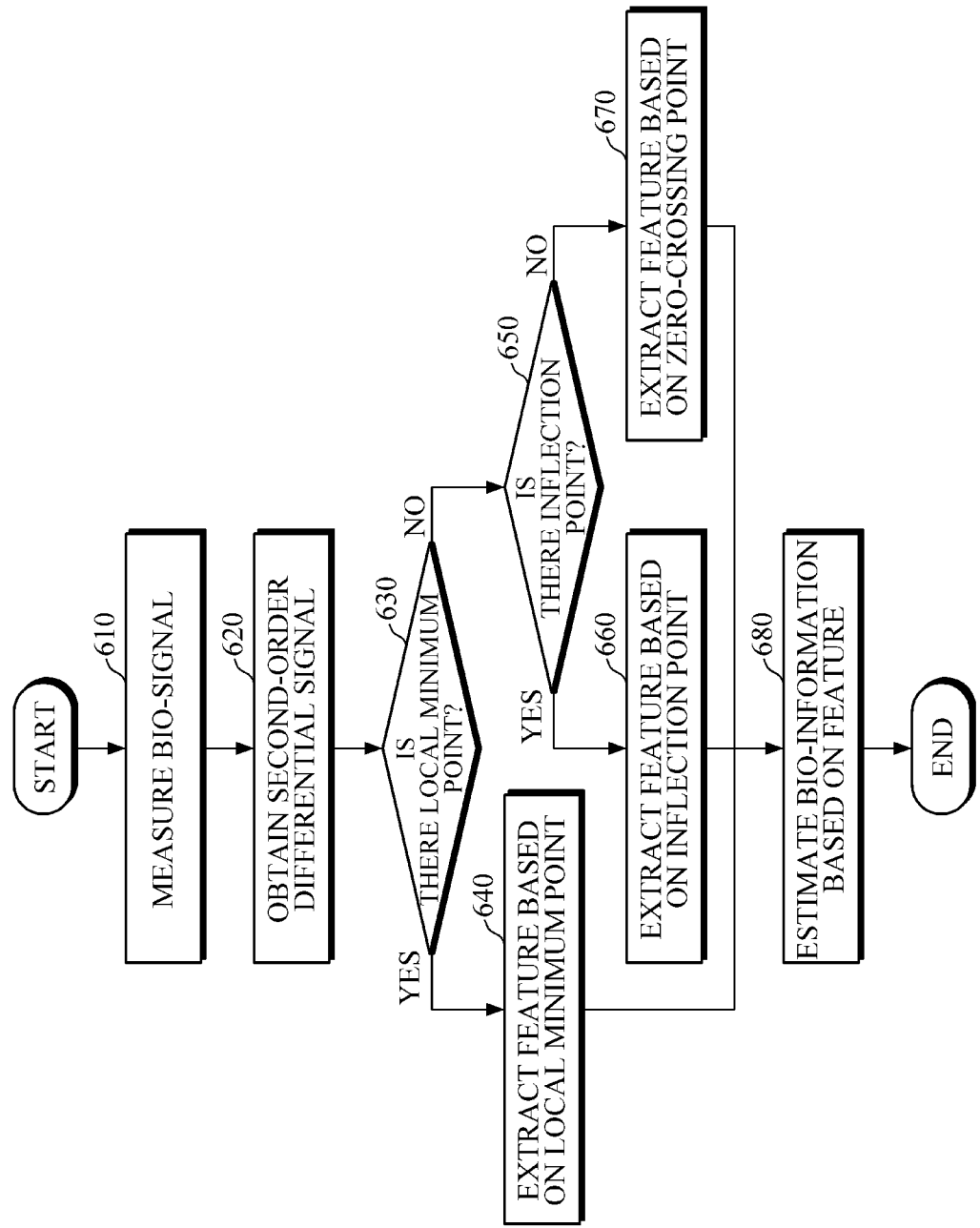
FIG. 6 is a flowchart illustrating a method of estimating bio-information according to another example embodiment.

FIG. 6 is a flowchart illustrating a method of estimating bio-information according to another example embodiment.

The method of FIG. 6 is an example of a method of estimating bio-information by an apparatus for estimating bio-information according to an example embodiment, and may be performed by any one of the apparatuses 100 and 200 for estimating bio-information according to the example embodiments of FIGS. 1 and 2.

Upon receiving a request for estimating bio-information, the apparatus for estimating bio-information according to an example embodiment may measure a bio-signal from an object in 610.

The apparatus for estimating bio-information according to an example embodiment may obtain a second-order differential signal by performing second-order differentiation on the measured bio-signal in 620.

The apparatus for estimating bio-information according to an example embodiment may obtain a local minimum point in a predetermined period of the second-order differential signal in 630. In this case, the predetermined period may be a systolic phase. For example, the apparatus for estimating bio-information according to an example embodiment may determine whether there is a local minimum point in an interval which is obtained by dividing a one-period interval of the entire PPG signal at a predetermined ratio (e.g., 1/5), but is not limited thereto.

Next, upon detecting the local minimum point in 630, the apparatus for estimating bio-information according to an example embodiment may extract an amplitude of the bio-signal, which corresponds to a time of the detected local minimum point in the second-order differential signal, as a feature in 640.

On the other hand, if it is determined that there is no local minimum point in 630, the apparatus for estimating bio-information according to an example embodiment may detect an inflection point in a predetermined period of the second-order differential signal in 650. For example, the apparatus for estimating bio-information according to an example embodiment may detect a point, at which a waveform of the second-order differential signal changes from being concave "downward" to convex "upward" during a time interval between the first local maximum point and the first local minimum point of the second-order differential signal. To this end, the apparatus for estimating bio-information according to an example embodiment may obtain a fourth-order differential signal of the bio-signal, and a detect a specific time where an amplitude at the specific time of the fourth-order differential signal is greater than zero, and an amplitude at a subsequent time is less than zero. Upon detecting the specific time, the apparatus for estimating bio-information according to an example embodiment may detect a point in the second-order differential signal, corresponding to the detected time, as an inflection point.

The apparatus for estimating bio-information according to an example embodiment may extract a feature based on the detected inflection point in 660. For example, the apparatuses 100 and 200 for estimating bio-information may extract an amplitude of the bio-signal, which corresponds to the time of the inflection point in the second-order differential signal, as a feature.

If there is no inflection point detected in 650, the apparatus for estimating bio-information according to an example embodiment may detect a zero-crossing point in a predetermined period of the second-order differential signal, and may extract a feature based on the detected zero-crossing point in 670. For example, if predetermined criteria are satisfied based on at least one of a time difference between the first local maximum point and the first local minimum point of the second-order differential signal and/or a time difference between the first local minimum point and the second local maximum point, the apparatus for estimating bio-information according to an example embodiment may determine that there is a zero-crossing point. Further, upon detecting a specific point, at which an amplitude is 0, in a predetermined period of the second-order differential signal, the apparatus for estimating bio-information according to an example embodiment may extract the amplitude, corresponding to the detected time, as a feature from the bio-signal.

The apparatus for estimating bio-information according to an example embodiment may estimate bio-information in 680 based on the features extracted in 640, 660, or 670. In addition to the extracted features, the apparatus for estimating bio-information according to an example embodiment may extract additional features, and may estimate bio-information by applying the bio-information estimation model to the extracted features. Further, the apparatus for estimating bio-information according to an example embodiment may provide a bio-information estimation result for a user.

Figure 7:
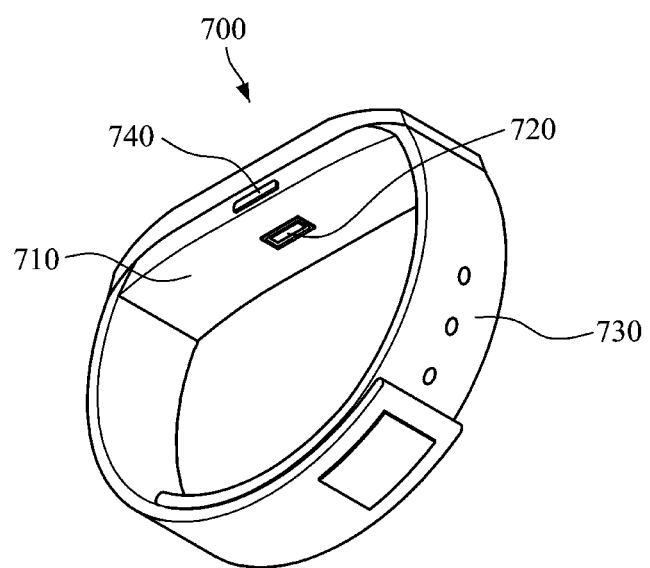
FIG. 7 is a diagram illustrating a wearable device according to an example embodiment.

FIG. 7 is a diagram illustrating a wearable device according to an example embodiment. The above example embodiments of the apparatus for estimating bio-information may be mounted in a smart watch worn on a wrist or a smart band-type wearable device, as illustrated in FIG. 7, but are not limited thereto.

Referring to FIG. 7, the wearable device 700 includes a main body 710 and a strap 730.

The main body 710 may be formed to have various shapes, and may include modules which are mounted inside or outside of the main body 710 to perform the aforementioned function(s) of estimating bio-information as well as various other functions. A battery may be embedded in the main body 710 and/or the strap 730 to supply power to various modules of the wearable device 700.

The strap 730 may be connected to the main body 710. The strap 730 may be flexible so as to be bent around a user's wrist. The strap 730 may be in a form such that the strap 730 is detachable from the main body 710 or may be formed as a band that is not detachable from the main body 710. Air may be injected into the strap 730 or an airbag may be included in the strap 730, so that the strap 730 may have elasticity according to a change in pressure applied to the wrist, and the change in pressure of the wrist may be transmitted to the main body 710.

The main body 710 may include a sensor 720 for measuring a bio-signal. The sensor 720 may be mounted on a rear surface of the main body 710, which comes into contact with the upper portion of a user's wrist, and may include a light source for emitting light onto the skin of the wrist and a detector for detecting light scattered or reflected from the object. The sensor 720 may further include a contact pressure sensor for measuring contact pressure applied by the object.

A processor may be mounted in the main body 710. The processor may be electrically connected to various modules, mounted in the wearable device 700, to control operations thereof. Further, the processor may estimate bio-information by using bio-signals measured by the sensor 720.

For example, the wearable device 700 may be worn on the wrist and measure a bio-signal from a capillary portion on an upper part of the wrist, thus acquiring a bio-signal mainly having low frequency components. Accordingly, as described above, the processor may first detect an inflection point in a predetermined period of a second-order differential signal of the bio-signal, and if there is no inflection point detected, the processor may detect a zero-crossing point in a predetermined period of the second-order differential signal of the bio-signal. However, the processor is not limited thereto, and may detect one of a local minimum point, an inflection point, and a zero-crossing point from a predetermined period of the second-order differential signal of the bio-signal based on various settings, and may extract features, which are associated with a first waveform component and are used for estimating bio-information.

In the case where the processor includes a contact pressure sensor, the processor may monitor a contact state of the object based on contact pressure between the wrist and the sensor 720, and may provide guide information on a contact position and/or a contact state for a user through a display.

Further, the main body 710 may include a storage which stores a processing result of the processor and a variety of information. In this case, the variety of information may include reference information related to estimating bio-information, as well as information associated with functions of the wearable device 700.

In addition, the main body 710 may also include a manipulator 740 which receives a user's control command and transmits the received control command to the processor. The manipulator 740 may include a power button to input a command to turn on/off the wearable device 700.

A display (not shown) may be mounted on a front surface of the main body 710, and may include a touch panel for receiving a touch input. The display may receive a touch input from a user, may transmit the received touch input to the processor, and may display a processing result of the processor. For example, the display may display a bio-information estimation value and related information (e.g., warning and/or alarm information).

A communication interface may be provided for communication with an external device such as a user's mobile terminal, and may be mounted in the main body 710. The communication interface may transmit an estimation result of bio-information to an external device, e.g., a user's smartphone, to display the result to the user. However, the communication interface is not limited thereto, may transmit and receive various types of necessary information.

Figure 8:
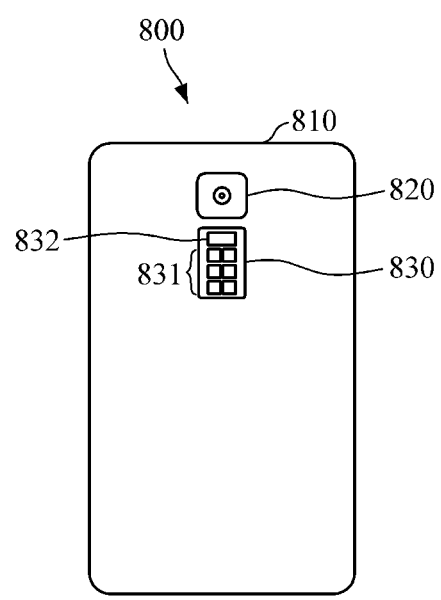
FIG. 8 is a diagram illustrating a smart device according to an example embodiment.

FIG. 8 is a diagram illustrating a smart device according to an example embodiment. The smart device according to an example embodiment may include a smartphone, a tablet PC, and the like, and may include any one of the apparatuses 100 and 200 for estimating bio-information according to example embodiments described above.

Referring to FIG. 8, the smart device 800 includes a main body 810 and a sensor 830 mounted on a surface of the main body 810. In this case, the sensor 830 may include a pulse wave sensor including at least one or more light sources 831 and a detector 832. As illustrated in FIG. 8, the sensor 830 may be mounted on a rear surface of the main body 810, but is not limited thereto. For example, the sensor 830 may be configured in combination with a fingerprint sensor or a touch panel mounted on a front surface of the main body 810.

In addition, a display may be mounted on a front surface of the main body 810. The display may visually display a bio-information estimation result and the like. The display may include a touch panel, and may receive a variety of information input through the touch panel and transmit the received information to the processor.

Additionally, an image sensor 820 may be mounted in the main body 810. When a user's finger approaches the sensor 830 to measure a pulse wave signal, the image sensor 820 may capture an image of the finger and may transmit the captured image to the processor. Based on the image of the finger, the processor may identify a relative position of the finger with respect to an actual position of the sensor 830, and may provide the relative position of the finger to the user through the display, so as to guide measurement of pulse wave signals with improved accuracy.

As described above, the processor may estimate bio-information based on bio-signals measured by the sensor 830. In this case, as described above, the processor may perform second-order differentiation on the bio-signal, and may obtain features, to be used for estimating bio-information, by detecting a local minimum point, an inflection point, and/or a zero-crossing point, in a predetermined period of the second-order differential signal. A detection order of characteristic points may be predetermined based on various conditions and the disclosure is not limited to any certain order. In this case, as the bio-signal is measured from a user's finger by using the sensor 830 mounted on the rear surface of the smart device 800, the processor may first detect the local minimum point, and may detect the inflection point and the zero-crossing point, but is not limited thereto.

The disclosure can be implemented as a computer-readable code written on a computer-readable recording medium. The computer-readable recording medium may be any type of recording device in which data is stored in a computer-readable manner.

Examples of the computer-readable recording medium include a ROM, a RAM, a CD-ROM, a magnetic tape, a floppy disc, an optical data storage, and a carrier wave (e.g., data transmission through the Internet). The computer-readable recording medium can be distributed over a plurality of computer systems connected to a network so that a computer-readable code is written thereto and executed therefrom in a decentralized manner. Functional programs, codes, and code segments needed for implementing the disclosure can be easily deduced by one of ordinary skill in the art.

According to example embodiments, methods and apparatuses for estimating bio-information may extract features in a stable and effective manner and estimate bio-information based on the extracted features, thereby improving accuracy in estimating bio-information.

At least one of the components, elements, modules or units described herein may be embodied as various numbers of hardware, software and/or firmware structures that execute respective functions described above, according to an example embodiment. For example, at least one of these components, elements or units may use a direct circuit structure, such as a memory, a processor, a logic circuit, a look-up table, etc. that may execute the respective functions through controls of one or more microprocessors or other control apparatuses. Also, at least one of these components, elements or units may be specifically embodied by a module, a program, or a part of code, which contains one or more executable instructions for performing specified logic functions, and executed by one or more microprocessors or other control apparatuses. Also, at least one of these components, elements or units may further include or implemented by a processor such as a central processing unit (CPU) that performs the respective functions, a microprocessor, or the like. Two or more of these components, elements or units may be combined into one single component, element or unit which performs all operations or functions of the combined two or more components, elements of units. Also, at least part of functions of at least one of these components, elements or units may be performed by another of these components, element or units. Further, although a bus is not illustrated in the block diagrams, communication between the components, elements or units may be performed through the bus. Functional aspects of the above example embodiments may be implemented in algorithms that execute on one or more processors. Furthermore, the components, elements or units represented by a block or processing steps may employ any number of related art techniques for electronics configuration, signal processing and/or control, data processing and the like.

The disclosure has been described herein with regard to example embodiments. However, it will be obvious to those skilled in the art that various modifications may be made without departing from the gist of the disclosure. Therefore, it is to be understood that that the scope of the disclosure is not limited to the above-mentioned embodiments, but is intended to include various modifications and equivalents included within the spirit and scope of the appended claims.

What is claimed is:

1. An apparatus for estimating bio-information, the apparatus comprising:
   a sensor configured to obtain a bio-signal from an object; and
   a processor configured to:
      obtain a second-order differential signal of the bio-signal;
      based on detection of an inflection point in a predetermined period of the second-order differential signal, extract a first feature based on the detected inflection point, and estimate bio-information based on the extracted first feature; and
      based on the inflection point not being detected in the predetermined period of the second-order differential signal, and further based on the predetermined period of the second-order differential signal satisfying at least one predetermined criterion, extract a second feature based on a zero-crossing point that is detected in the predetermined period of the second-order differential signal, and estimate the bio-information based on the extracted second feature,
   wherein the at least one predetermined criterion comprises at least one of:
   a first criterion as to whether a first value, obtained by subtracting a time corresponding to a first local maximum point of the second-order differential signal from a time corresponding to a first local minimum point of the second-order differential signal, is greater than a first threshold; or
   a second criterion as to whether the first value is greater than a value, obtained by multiplying a second value with a second threshold, the second value being obtained by subtracting the time corresponding to the first local minimum point from a time corresponding to a second local maximum point of the second-order differential signal.

2. The apparatus of claim 1, wherein the processor is configured to, based on the inflection point not being detected in the predetermined period of the second-order differential signal, and further based on the predetermined period of the second-order differential signal not satisfying the at least one predetermined criterion, extract a third feature based on the first local minimum point of the second-order differential signal, and estimate the bio-information based on the extracted third feature.

3. The apparatus of claim 1, wherein the sensor comprises a pulse wave sensor, and the pulse wave sensor comprises a light source and a detector, the light source being configured to emit light onto the object, and the detector being configured to detect the light emitted onto the object and reflected or scattered from the object.

4. The apparatus of claim 1, wherein the predetermined period comprises a time interval between the first local maximum point and the first local minimum point of the second-order differential signal.

5. The apparatus of claim 1, wherein the inflection point is a point, at which a waveform of the second-order differential signal changes from being concave downward to being convex upward with respect to a time axis of the second-order differential signal.

6. The apparatus of claim 1, wherein the processor is further configured to obtain a fourth-order differential signal of the bio-signal, detect a first time point in a predetermined period of the fourth-order differential signal, an amplitude at the first time point in the fourth-order differential signal being greater than zero and an amplitude at a second time point after the first time point being less than zero, and to detect a point of the second-order differential signal, which corresponds to the first time point, as the inflection point.

7. The apparatus of claim 1, wherein the processor is further configured to extract an amplitude of the bio-signal, which corresponds to the inflection point, as the first feature.

8. The apparatus of claim 1, wherein the processor is further configured to extract, as the second feature, an amplitude of the bio-signal which corresponds to at least one of the zero-crossing point, an internally dividing point between the zero-crossing point and a start point of the predetermined period, and an internally dividing point between the zero-crossing point and an end point of the predetermined period.

9. The apparatus of claim 1, wherein the bio-information comprises a blood pressure.

* * * * *